United States Patent [19]

Pearson

[11] 4,229,541
[45] Oct. 21, 1980

[54] IN VITRO CULTIVATION OF HORSESHOE CRAB AMEBOCYTES

[75] Inventor: Frederick C. Pearson, Lake Zurich, Ill.

[73] Assignee: Baxter Travenol Laboratories, Inc., Deerfield, Ill.

[21] Appl. No.: 949,009

[22] Filed: Oct. 6, 1978

[51] Int. Cl.³ .............................................. C12N 5/02
[52] U.S. Cl. .................................................... 435/241
[58] Field of Search ................................. 435/240, 241

[56] References Cited

U.S. PATENT DOCUMENTS

| | | | |
|---|---|---|---|
| 3,039,932 | 6/1962 | McLimans et al. | 435/240 |
| 3,128,228 | 4/1964 | Michl | 435/240 |
| 3,275,528 | 9/1966 | Ainis | 435/240 |
| 3,432,595 | 3/1969 | Kasza | 435/240 |
| 3,854,470 | 12/1974 | Augspurger | 435/240 |
| 3,862,002 | 1/1975 | Sanders | 435/240 |
| 3,906,929 | 9/1975 | Augspurger | 435/240 |
| 3,997,396 | 12/1976 | Delente | 435/240 |

OTHER PUBLICATIONS

Sanhorn et al., Biol. Bull., vol. 117, p. 399, 1959.
Wolff, Bull. Soc. Zool. France, vol. 87, pp. 120–126; 1962.
Loeb et al., Am. Journal of Physiology, vol. 60, pp. 277–301, 1922.
Loeb, J. Med. Res., vol. 7, pp. 145–158, 1902.
Loeb et al., Journal of Biol. Chem., vol. 67, pp. 79–90, 1926.
Yamamichi et al., Dev Growth and Diff, vol. 16, No. 4, pp. 295–304, 1974.

Primary Examiner—Robert J. Warden
Attorney, Agent, or Firm—Paul C. Flattery; Lawrence W. Flynn; Max D. Hensley

[57] ABSTRACT

A culture medium for cultivating horseshoe crab amebocytes, called Limulus amebocytes, composed of inorganic salts, vitamins, amino acids, and carbon sources including glucose is given. The process for cultivating the Limulus amebocytes depends on maintaining a pH between 6.5 and 9.0 while agitating the medium. Production of Limulus lysate from these cells is an eventual goal.

4 Claims, No Drawings

IN VITRO CULTIVATION OF HORSESHOE CRAB AMEBOCYTES

BACKGROUND

It has been observed that amebocyte lysate from *Limulus polyphemus*, the horseshoe crab, coagulates in the presence of small amounts of endotoxin. Additionally, the Limulus lysate test has been used to detect gram-negative septicemia in humans. This test has been adapted for the rapid detection of endotoxins in radiopharmaceuticals and biologicals. Bacteriuria due to gram-negative bacteria can be diagnosed by the Limulus test, which appears promising for screening large populations for urinary tract infections. Also, endotoxin levels in drinking water have been defined by use of the Limulus assay. Rapid detection of gram-negative bacterial meningitis by the Limulus test is discussed in U.S. Pat. No. 4,067,776 to Waheed Kahn. Methods for detecting endotoxins with Limulus lysate are given in U.S. Pat. Nos. 3,915,805; 3,944,391; and 4,038,147.

Preparation of Limulus lysate is given in U.S. Pat. No. 3,954,663 and the method of diagnosis is discussed by Kahn (supra).

There is little question that the Limulus lysate test has great potential in various activities, including medicine and industry. However, it has not been endorsed by the Food and Drug Administration for use in clinical detection of endotoxin. One major reason is lysate variability. Quality of lysate fluctuates with individual crabs, and exhibits batch and seasonal variabilities. Presently, the production of lysate declines around the first of September, as supplies of horseshoe crabs dwindle, and ceases through the fall, winter, and late spring.

Although the production and application of the Limulus Amebocyte Lysate test has become more standardized in recent years, experience still supports the notion that significant variation occurs in lysate produced by various manufacturers and that lot-to-lot variation is exhibited by individual manufacturers. Despite the use of a standard endotoxin, a reference lysate and the widespread use of the clot endpoint, the problem of lysate variability remains. The successful cultivation of Limulus amebocytes in the laboratory suggests the possibility of producing a lysate that is not subject to the variability of the natural environment. Such a standardized production would most probably reduce batch variability and seasonal variability of lysate. Bleeding of horseshoe crabs might be deleted and thus the collection, transportation and possible depletion of the horseshoe crab population could be circumvented.

Transportation of the crab presents a problem, and if a current practice employed is continued, bleeding and returning captive animals to the ocean is also a problem. There is, of course, some question whether the weakened crabs survive. With large numbers of crabs being used for production of Limulus lysate, serious depletion of the horseshoe crab population must be considered a real possibility.

Another difficulty encountered in bleeding the horseshoe crabs is the possibility of contaminating the lysate.

While in vitro cultivation of a number of cell types from Limulus tissues has been maintained up to 30 days, it was noted that after 10 days vacuolation and granulation became pronounced. Clotted blood of Limulus as an explant maintained amebocytes for 3 months, but there was no cell migration from explant to medium.

Therefore it is an object of the present invention to develop a standard source of cells for eventual standardized production of Limulus lysate.

Additionally, it is an object of the present invention to provide a medium and process for growing Limulus amebocytes.

A further object of the present invention is to provide a readily available source of Limulus amebocytes for Limulus lysate.

Another object of the present invention is to provide standardized Limulus amebocytes for Limulus lysate tests in accordance with FDA criteria for routine diagnostic use for endotoxin detection.

Additionally, it is the object of the present invention to provide a medium suitable for cultivating a number of tissues from marine invertebrates such as lobsters and crabs as well as marine fishes. Additional objects and advantages of the present invention will be apparent to those skilled in the art by reference to the following detailed description.

Limulus amebocytes may be cultivated in vitro by using a basal medium consisting of various amino acids, carbon sources, inorganic salts and vitamins. Sodium chloride is used to simulate isotonic conditions encountered in the natural environment of the amebocyte. Significant amounts of divalent cations of magnesium and calcium are used and an inorganic buffer system is established with sodium bicarbonate and dihydrogen sodium phosphate. Inorganic sulfate and phosphate are employed to provide phosphorus and sulfur for biosynthesis of organo-phospho and organo-sulfur compounds such as nucleic acid bases and amino acids. Amino acids are incorporated in the medium from the following groups of amino acids; aromatic, sulfur containing, aliphatic, monoamino, dicarboxylic and diamino carboxylic acids. A number of common vitamins are also used. Nucleic acid bases may also be used. A number of carbon sources may be used but glucose is sufficient.

Amebocytes can be cultivated at a wide variety of temperatures ranging from 10°–40° C. but optimal range is at ambient laboratory temperature (20°–30° C.). Cells can grow at pH values ranging from acid to alkaline conditions. However, alkaline conditions are preferred. pHs above 7 and below 8.5 are preferred, but pHs from 6.5 to 9 are possible.

Cells cultivated at temperatures between 12°–24° C. produce the greatest cell growth. Amebocytes grown at 37° C. were severely inhibited and cell yields obtained at 4° C. were less than those at room temperature.

These cells can be cultivated in most kinds of cell culture chambers and on all cell culture materials tested, i.e., various glass and plastic products. A spinner culture is most appropriate in which an inoculum of 0.1 ml of amebocytes per 50 ml of medium is placed in an appropriate sized vessel and agitated slowly with a stirring device. Oxygen is made available through a loosened cap or a cotton plugged port. Small vessels or large vessels are appropriate for such cultures provided sufficient inoculum is used. Amebocytes which have been cultivated in vitro may be used for inocula for subsequent media in a continuous fashion.

All glassware is rendered pyrogen-free by treating with 1% E-toxaclean (Sigma Chemical Company, St. Louis, Missouri) overnight and washing with sterile pyrogen-free distilled water. Falcon plastic pipettes are used for all work. Larger borosilicate bottles, such as the 500 ml size, may also be used. Cells that have been cultivated in vitro may be used as an innoculum at the ratio of 0.1 ml of cells to 50 ml of medium. In this way amebocytes from the original culture can be cultivated through an indefinite number of passages.

The culture media are modified basal media composed of salts, amino acids, sugars and vitamins. PAM (Pearson's Amebocyte Medium) is preferred. MEM (Modified Essential Medium) is commercially available, but less effective. The composition is given below.

TABLE I

| Component | mg/L (PAM) | (MEM) |
|---|---|---|
| Inorganic salts | | |
| NaCl | 1000 | 6800 |
| CaCl$_2$ | 30 | 200 |
| KCl | 30 | 400 |
| MgCl$_2$ . 6H$_2$O | 2280 | — |
| MgSO$_4$ . 7H$_2$O | 2780 | 200 |
| NaHCO$_3$ | 350 | 2200 |
| NaH$_2$PO$_4$ . H$_2$O | 1013 | 140 |
| OTHER COMPONENTS | | |
| Alpha-Ketoglutaric acid | 370 | |
| Glucose | 1000 | |
| Malic acid | 670 | |
| Sodium pyruvate | — | 110 |
| Lipoic acid | — | 0.02 |
| AMINO ACIDS | | |
| L-Alanine | 225 | 25 |
| L-Arginine HCl | 700 | 126.9 |
| L-Asparagine | 350 | 25 |
| L-Aspartic acid | 350 | 30 |
| L-Cystine | 100 | 24 |
| L-Glutamic acid | 600 | 75 |
| L-Glutamine | 600 | 292 |
| Glycine | 650 | 72.47 |
| L-Histidine | 2500 | 42 |
| L-Isoleucine | 50 | 52.50 |
| L-Leucine | 75 | 52.40 |
| L-Lysine HCl | 625 | 58 |
| L-Methionine | 50 | 15 |
| L-Phenylalanine | 150 | 32 |
| L-Proline | 350 | 40 |
| DL-Serine | 1100 | 25 |
| L-Threonine | 175 | 48 |
| L-Trytophane | 100 | 10 |
| L-Tyrosine | 50 | 36 |
| L-Cysteine HCl . H$_2$O | — | 100 |
| L-Valine | 100 | — |
| VITAMINS | | |
| Biotin | 0.01 | 0.10 |
| D-Ca pantothenate | 0.02 | 1.00 |
| Choline chloride | 0.20 | 1.00 |
| Folic acid | 0.02 | 1.00 |
| i-Inositol | 0.02 | 2.00 |
| Niacin | 0.02 | 1.00 |
| Para-aminobenzoic acid | 0.02 | — |
| Pyridoxine HCl | 0.02 | 1.0 |
| Riboflavin | 0.02 | 0.1 |
| Thiamine HCl | 0.02 | 1.0 |
| L-Ascorbic acid | — | 50.0 |
| Vitamin B$_{12}$ | — | 1.36 |
| NaOH to make pH 7.1-7.4 or other suitable base | | |

A culture medium may also be obtained by making a variety of substitutions and additions to Grace's insect TC medium, available from Sigma Chemical Co., St. Louis, Missouri. The additions to Grace's insect medium (GIM) are as follows:

Glucose: 1000 mg/L
KCl: 30 mg/L
CaCl$_2$: 30 mg/L
NaCl: 1000 mg/L
L-cystine: 100 mg/l The following ingredients are deleted, fructose, frumaric acid, succinic acid, sucrose, and B-alanine. Additionally, the medium must be adjusted to a basic pH with sodium hydroxide.

It has also been found preferable to incorporate 10% of horseshoe crab serum. It will be appreciated that sugars, proteins, lipids, enzymes, other electrolytes and trace elements may well increase growth. It has, however, been found that protein supplements commonly used to promote growth in cell cultures were found to be generally inhibitory to amebocytes, e.g., fetal calf serum, horse serum, albumin, yeastolate and lactalbumin hydrolysate.

Amebocytes are cultivated in graduated 500 ml borosilicate bottles by centrifugation 50 Xg for ten minutes and then transferred to a 50 ml polypropylene centrifuge tube and washed once. Then cells are centrifuged again and lysed with pyrogen-free distilled water using a ratio of 1:3 packed cells to water. Ratios of up to 1:6 packed cells to water is also acceptable for a lysing ratio. Cells are then suspended by using a Vortex Genie mixer and storing the tubes at 4° C. for 24 hours. In addition, cell harvests may be freeze-thawed twice to release lysate from the amebocytes. Lysate is harvested the next day by centrifugation at 150 Xg ten minutes and collecting the supernatant. Since an anti-clotting agent is not always required for amebocytes generated in vitro, a single wash in 3% pyrogen-free sodium chloride is sufficient.

If clotting of amebocytes occurs as it does with naturally harvested horseshoe crab blood cells, in vitro cultivated cells may be prepared by mixing equal volumes of amebocytes in 0.125% N-ethyl malemide which is dissolved in pyrogen-free 3% sodium chloride. Amebocytes must then be centrifuged at 50 Xg gravity for ten minutes and subsequently washed twice in 3% sodium chloride which is pyrogen-free. Lysate would then be harvested as above using distilled water and/or a freeze-thaw method for lysate release.

Cell growth can be monitored by total cell count using an American optical hemocytometer and total DNA by using a modified Dische method or by employing a Lowry protein determination.

The supplemental horseshoe crab serum, which increases the growth of cells was prepared by collecting crab blood in 500 ml pyrogen-free bottles, allowing clot formation to take place at 4° C. overnight, subsequently harvesting the dark blue supernatant and clarifying by centrifugation. Serum was filter sterilized prior to use and routinely employed in cultures at 10%. Tests demonstrated the following components in horseshoe crab serum.

Inorganic phosphate: 1.1 mg%
Glucose: 24.0 mg%
Blood Urea Nitrogen: 1.9 mg%
Uric Acid: 0.6 mg%
Cholesterol: 10.0 mg%
Total Protein: 4.9 g%
Albumin: 2.7 g%
Bilirubin: 0.1 mg%
Alkaline Phosphatase: 18.0 mu/ml
Lactic acid dehydrogenase: 40 mu/ml
Serum glutamic oxalactic Transaminase: 50 mu/ml
Calcium: 320 mg/ml
Magnesium: 349 mg/ml
Total Protein: 6.09%
Albumin: 4.02 g%

The following examples illustrate the invention.

EXAMPLE 1

Horseshoe crabs are bled by introducing a 14-gauge needle into the cardiac chamber and withdrawing sufficient inoculum into a 5-cc heparinized syringe to inoculate 0.1 ml of cells per 50 ml of medium using PAM medium shown in Table I. The amebocytes are cultivated in a 50 ml borosilicate glass bottle placed on a magnetic stirring device and using a ⅛ inch teflon-coated, siliconized stirring bar. The cells are cultivated in a Warren-Sharer environmental chamber at 25° C. and pH 7.1. The pH is maintained between 7.1 and 7.5, and the temperature between 21° to 25° C.

EXAMPLE 2

The procedure of Example 1 was followed with the single exception that MEM medium shown in Table I was employed. The medium is adjusted to a pH of 7.1 and the temperature is maintained between 21° to 25° C. The total cell yield is less using this medium than the medium in Example 1.

EXAMPLE 3

The procedure of Example 1 is followed, employing PAM medium and in addition, 10% of horseshoe crab serum by weight per medium. The horseshoe crab serum is prepared by bleeding adult horseshoe crabs with a non-pyrogenic, siliconized #14 gauge needle which is inserted into the cardiac chamber. The hemolymph (blood and serum) is allowed to flow into appropriate container and subsequently allowed to stand at 4° C. for a few hours or overnight. A clot will form and retract from the serum. The preparation is then centrifuged sufficiently to pellet clot. Serum is then decanted into depyrogenated borosilicate glass and stored at −25° C. until incorporated into culture medium. This gives the best cell yield.

EXAMPLE 4

Cell crops from Example 1 were harvested in pyrogen-free, siliconized, 250 ml polypropylene centrifuge bottles containing 125 ml of 0.125% N-ethyl maleimide in 3% sodium chloride at pH 7.4. Cells are centrifuged at 50 Xg for 10 minutes, washed twice in 3% sodium chloride and then lysed in distilled water 1:3 at 4° C. for 18-24 hours. Cells are then vortexed for one minute and centrifuged at 100 Xg for 10 minutes to clarify the cell lysate. The supernatant is decanted and stored at 70° C.

Lysate preparations are tested for potency by using graded endotoxin solutions ranging from 1.0 pg to 1000 ng per ml. Since solid clots were not formed by lysate preparations, a graded endpoint was used ranging from 0 (negative) to +3 (a clot that would run when the tube was tilted 180°). Intermediate values were based on degree of opacity, viscosity and production of floccules. To date, lysate preparations from amebocytes grown in vitro have given only slight positive results (+1 reaction) in the presence of 1000 ng of endotoxin.

Although the invention has been described in considerable detail with reference to certain preferred embodiments thereof, it will be understood that variations and modifications can be affected within the spirit and scope of the invention as described above and as defined in the appended claims.

What is claimed is:

1. A culture medium for cultivating Limulus amebocytes, comprising glucose, L-cystine, salts, vitamins, amino acids and horseshoe crab serum.

2. A culture medium for cultivating Limulus amebocytes in vitro comprising horseshoe crab serum and:
NaCl: 1000 mg/L
CaCl$_2$: 30.0
KCl: 30.0
MgCl$_2$.6H$_2$O: 2280.
MgSO$_4$.7H$_2$O: 2780.
NaHCO$_3$: 350
NaH$_2$PO$_4$.H$_2$O: 1013.0
alpha Ketoglutaric acid: 370.
Glucose: 1000.
Malic acid: 670
L-alanine: 225
L-Arginine HCl: 700.0
L-Asparagine: 350.00
L-Aspartic acid: 350.0
L-Cystine: 100.
L-Glutamic acid: 600.00
L-Glutamine: 600.00
Glycine: 650.00
L-Histidine: 2500.00
L-Isoleucine: 50.00
L-Leucine: 75.00
L-Lysine HCl: 625.00
L-Methionine: 50.00
L-Phenylalinine: 150.00
L-Proline: 350.00
DL-Serine: 1100.00
L-Threonine: 175.00
L-Tryptophane: 100.00
L-Tyrosine: 50.00
L-Valine: 100.0
VITAMINS
Biotin: 0.01
D-Ca pantothenate: 0.02
Choline chloride: 0.20
Folic acid: 0.02
i-Inositol: 0.02
Niacin: 0.02
Para-aminobenzoic acid: 0.02
Pyridoxine HCl: 0.02
Riboflavin: 0.02
Thiamine HCl: 0.02.

3. A process for propagating Limulus amebocytes in vitro, comprising inoculating Limulus amebocytes into a nutrient medium comprising a carbon source, salts, vitamins, amino acids and horseshoe crab serum, constantly agitating the suspension of amebocytes in the medium at a temperature of from 12° C. to 30° C., and isolating the amebocytes from the suspension.

4. A process of claim 3 wherein the nutrient medium is composed of horseshoe crab serum and:
NaCl: 1000 mg/L
CaCl$_2$: 30.0
KCl: 30.0
MgCl$_2$.6H$_2$O: 2280.
MgSO$_4$.7H$_2$O: 2780.
NaHCO$_3$: 350
NaH$_2$PO$_4$.H$_2$O: 1013.0
alpha Ketoglutaric acid: 370.
Glucose: 1000.
Malic acid: 670
L-Alanine: 225
L-Arginine HCl: 700.0
L-Asparagine: 350.00
L-Aspartic acid: 350.0
L-Cystine: 100.
L-Glutamic acid: 600.00
L-Glutamine: 600.00
Glycine: 650.00
L-Histidine: 2500.00
L-Isoleucine: 50.00

L-Leucine: 75.00
L-Lysine HCl: 625.00
L-Methionine: 50.00
L-Phenylalinine: 150.00
L-Proline: 350.00
DL-Serine: 1100.00
L-Threonine: 175.00
L-Tryptophane: 100.00
L-Tyrosine: 50.00
L-Valine: 100.0
VITAMINS
Biotin: 0.01
D-Ca pantothenate: 0.02
Choline chloride: 0.20
Folic acid: 0.02
i-Inositol: 0.02
Niacin: 0.02
Para-aminobenzoic acid: 0.02
Pyridoxine HCl: 0.02
Riboflavin: 0.02
Thiamine HCl: 0.02.

* * * * *